(12) United States Patent
Yagihashi et al.

(10) Patent No.: US 11,472,753 B2
(45) Date of Patent: Oct. 18, 2022

(54) METHOD FOR PRODUCING 1,3-BUTADIENE

(71) Applicant: SEKISUI CHEMICAL CO., LTD., Osaka (JP)

(72) Inventors: Noritoshi Yagihashi, Ibaraki (JP); Haruka Nishiyama, Ibaraki (JP); Yuki Nakama, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 17/623,756

(22) PCT Filed: Jul. 6, 2020

(86) PCT No.: PCT/JP2020/026485
§ 371 (c)(1),
(2) Date: Dec. 29, 2021

(87) PCT Pub. No.: WO2021/006252
PCT Pub. Date: Jan. 14, 2021

(65) Prior Publication Data
US 2022/0204424 A1 Jun. 30, 2022

(30) Foreign Application Priority Data

Jul. 5, 2019 (JP) .............................. JP2019-126001

(51) Int. Cl.
*C07C 1/24* (2006.01)
*B01D 3/14* (2006.01)
*C07C 7/04* (2006.01)

(52) U.S. Cl.
CPC ................ *C07C 1/24* (2013.01); *B01D 3/143* (2013.01); *C07C 7/04* (2013.01)

(58) Field of Classification Search
CPC ........... C07C 11/167; C07C 5/48; C07C 7/11; C07C 7/005; C07C 1/20; C07C 1/2076;
(Continued)

(56) References Cited

U.S. PATENT DOCUMENTS

2017/0291859 A1* 10/2017 Dastillung ............ C07C 1/2076

FOREIGN PATENT DOCUMENTS

| EP | 3 995 475 | 5/2022 |
| JP | 2013-516487 | 5/2013 |

(Continued)

OTHER PUBLICATIONS

Decision to Grant a Patent dated Aug. 17, 2021 in Japanese Application No. 2020-550183, with English translation.
(Continued)

*Primary Examiner* — Sharon Pregler
(74) *Attorney, Agent, or Firm* — Wenderoth, Lind & Ponack, L.L.P.

(57) ABSTRACT

In the method of the present invention, 1,3-butadiene is produced by vaporizing an ethanol feedstock in a vaporizer (104), feeding the resulting into two or more parallel first reactors (108) to convert the ethanol to acetaldehyde in the presence of a first catalyst, supplying the resulting intermediate gas to a second reactor (110) to convert the ethanol and acetaldehyde to 1,3-butadiene in the presence of a second catalyst, purifying the resulting crude gas containing 1,3-butadiene by a gas-liquid separator (112), a first distillation column (114), a fourth reactor (116), a second distillation column (118), and mixing one of both of a part of the ethanol-containing gas and an acetaldehyde-containing gas obtained in the second distillation column (118) are mixed with the intermediate gas, thereby adjusting an ethanol/acetaldehyde molar ratio in the intermediate gas to 1 to 100.

5 Claims, 3 Drawing Sheets

(58) Field of Classification Search
CPC .......... C07C 7/08; C07C 7/09; B01J 23/8876; B01J 21/08; B01J 21/10; B01J 23/30; B01J 35/0006; B01J 35/1014; B01J 35/1019; B01J 35/1038; B01J 37/0201; B01J 37/0205; B01J 37/0244; B01J 37/0248; B01J 8/0278
See application file for complete search history.

(56) References Cited

FOREIGN PATENT DOCUMENTS

| | | |
|---|---|---|
| JP | 2015-34151 | 2/2015 |
| JP | 2017-532318 | 11/2017 |
| JP | 2018-87105 | 6/2018 |
| WO | 2011/085223 | 7/2011 |
| WO | 2016/111203 | 7/2016 |
| WO | 2016/136471 | 9/2016 |
| WO | 2018/073282 | 4/2018 |
| WO | 2018/178005 | 10/2018 |

OTHER PUBLICATIONS

International Search Report dated Sep. 8, 2020 in International (PCT) Application No. PCT/JP2020/026485.
Notice of Reasons for Rejection dated Jun. 30, 2020 in corresponding Japanese Patent Application No. 2019-126001, with English language translation.
Decision of Rejection dated Feb. 2, 2021 in corresponding Japanese Patent Application No. 2020-550183, with English language translation.
Extended European Search Report dated Aug. 5, 2022 in European Application No. 20836646.8.

* cited by examiner

METHOD FOR PRODUCING 1,3-BUTADIENE

TECHNICAL FIELD

The present invention relates to a method for producing 1,3-butadiene.

Priority is claimed on Japanese Patent Application No. 2019-126001, filed Jul. 5, 2019, the contents of which are incorporated herein by reference.

BACKGROUND ART

Butadiene such as 1,3-butadiene is used as a raw material for styrene-butadiene rubber (SBR) and the like. As a method for producing 1,3-butadiene, for example, a method of converting ethanol to acetaldehyde and further converting ethanol and acetaldehyde to 1,3-butadiene in the presence of a catalyst is known (Patent Document 1).

PRIOR ART REFERENCES

Patent Document

Patent Document 1: Japanese Unexamined Patent Application Publication (Translation of PCT Application) No. 2017-532318

DISCLOSURE OF INVENTION

Problems to be Solved by the Invention

However, the conventional production method leaves a room for improvement in the yield of 1,3-butadiene.

An object of the present invention is to provide a method for producing 1,3-butadiene that can continuously produce 1,3-butadiene in high yield.

Means to Solve the Problems

The embodiments of the present invention are as follows.
[1] A method for continuously producing 1,3-butadiene from an ethanol feedstock containing ethanol, including:
a gas preparation step of preparing an ethanol-containing gas from the ethanol feedstock; a conversion step of converting ethanol in the ethanol-containing gas to 1,3-butadiene in the presence of a catalyst; and a purification step of purifying a crude gas containing the 1,3-butadiene obtained in the conversion step to obtain a purified 1,3-butadiene,
wherein the gas preparation step comprises a step A1 of vaporizing the ethanol feedstock to obtain the ethanol-containing gas under a pressure of −1.0 to 1.0 MPaG and at a temperature of −100 to 200° C.,
the purification step comprises at least one step selected from the group consisting of: a step C1 of converting butene in the crude gas into 1,3-butadiene by dehydrogenation reaction; a step C2 of separating hydrogen gas from the crude gas by gas-liquid separation to obtain a 1,3-butadiene-containing liquid; a step C3 of distilling a liquefied product of the crude gas or the 1,3-butadiene-containing liquid to separate the liquefied product or the 1,3-butadiene-containing liquid into an ethylene-containing gas, a 1,3-butadiene-containing effluent, and an acetaldehyde-containing liquid; and a step C4 of distilling the acetaldehyde-containing liquid to separate the acetaldehyde-containing liquid into an acetaldehyde-containing gas and a residual liquid containing water, the conversion step includes a step B1 of supplying the ethanol-containing gas to a first reactor and converting ethanol into acetaldehyde in the presence of a first catalyst under a pressure of 0 to 1.0 MPaG and at a temperature of 50 to 500° C., a step B2 of supplying an intermediate gas containing ethanol and acetaldehyde obtained in the step B1 to a second reactor and converting the intermediate gas into 1,3-butadiene under a pressure of 0 to 1.0 MPaG and at a temperature of 50 to 500° C. in the presence of a second catalyst, and a step B3 of mixing one or both of a part of the ethanol-containing gas obtained in the step A1 and the acetaldehyde-containing gas obtained in the step C4 with the intermediate gas, thereby adjusting an ethanol/acetaldehyde molar ratio in the intermediate gas to 1 to 100.
[2] The method according to [1], wherein an amount of either one or both of the ethanol-containing gas and the acetaldehyde-containing gas which are mixed with the intermediate gas in the step B3 is adjusted, based on results of monitoring the ethanol/acetaldehyde molar ratio in the intermediate gas supplied to the second reactor with an analyzer.
[3] The method according to [1] or [2], wherein the conversion step further includes a step B4 of separating hydrogen gas from the intermediate gas.
[4] The method according to any one of [1] to [3], wherein the intermediate gas is discharged from the first reactor, based on results of monitoring a hydrogen concentration in the first reactor by an analyzer.
[5] The method according to any one of [1] to [4], wherein the crude gas is discharged from the second reactor, based on results of monitoring a 1,3-butadiene concentration and a hydrogen concentration in the second reactor with an analyzer.
[6] The method according to any one of [1] to [5], wherein the gas preparation step further comprises a step A2 of mixing at least one type of gas with the ethanol-containing gas to adjust the concentration of ethanol in the ethanol-containing gas to fall within a range of 0.1 to 100% by volume.

Effect of the Invention

The present invention can provide a method for producing 1,3-butadiene that can continuously produce 1,3-butadiene in high yield.

DESCRIPTION OF EMBODIMENTS

Figure 1:
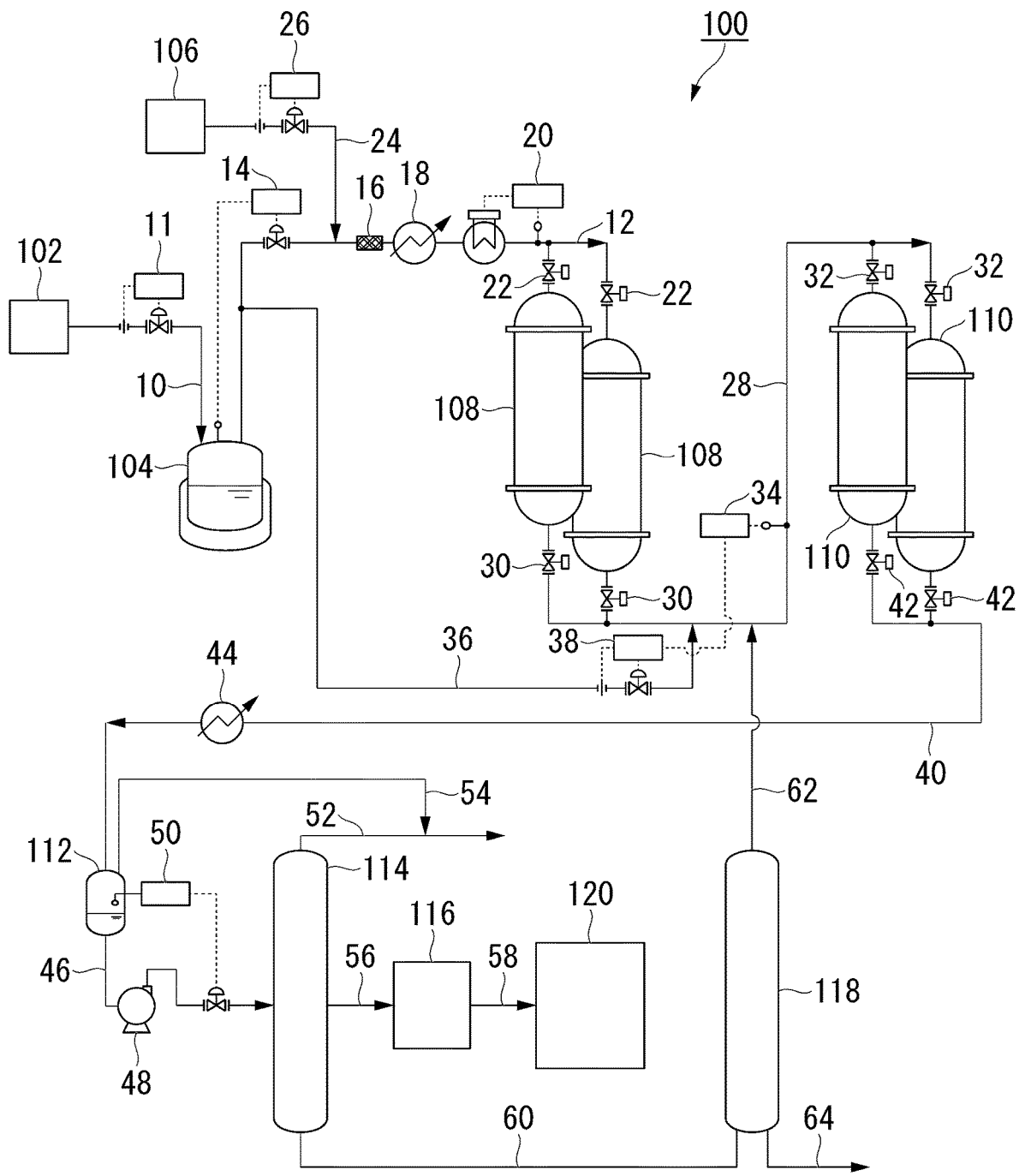
FIG. 1 is a schematic view showing a production apparatus used in the method for producing 1,3-butadiene according to the first embodiment.

The method of the present invention is a method for continuously producing 1,3-butadiene from an ethanol feedstock containing ethanol, which includes the following step A to step C. Further, the method of the present invention preferably further includes the following step D for improving the yield of 1,3-butadiene.

Step A: gas preparation step of preparing an ethanol-containing gas from the ethanol feedstock.

Step B: conversion step of converting ethanol in the ethanol-containing gas to 1,3-butadiene in the presence of a catalyst.

Step C: purification step of purifying a crude gas containing the 1,3-butadiene obtained in the step B to obtain a purified 1,3-butadiene.

Step D: catalyst regeneration step of regenerating the catalyst.

(Step A)

The step A includes a step A1 of vaporizing the ethanol feedstock to obtain the ethanol-containing gas under a pressure of −1.0 to 1.0 MPaG and at a temperature of −100 to 200° C.

In the context of the present specification, "to" indicating a numerical range means that the numerical values described before and after "to" are included as the lower limit and the upper limit of the range.

The ethanol feedstock contains ethanol as an essential component, and may contain other components such as water as long as the effects of the present invention are not impaired. The ratio of ethanol in the ethanol feedstock is preferably 80% by mass or more, more preferably 90% by mass or more, and even more preferably 93% by mass or more, based on the total mass of the ethanol feedstock. The upper limit of the ratio of ethanol is theoretically 100% by mass.

The ethanol feedstock is not particularly limited, and may be, for example, ethanol derived from fossil fuels such as shale gas and petroleum, or bioethanol derived from biomass such as plants, animals, and garbage. Of these, bioethanol is preferable because bioethanol contains less impurities such as nitrogen compounds and sulfur compounds and is less likely to cause catalyst deterioration.

The pressure for vaporization of the ethanol feedstock in the step A1 may be set in the range of −1.0 to 1.0 MPaG, preferably −0.5 to 0.5 MPaG, and more preferably −0.3 to 0.3 MPaG. When the pressure for vaporization of the ethanol feedstock is not lower than the lower limit of the above range, the volume of the gas resulting from the vaporization does not become excessive and the size of the equipment can be suppressed. When the pressure for vaporization of the ethanol feedstock is not higher than the upper limit of the above range, the ethanol feedstock is efficiently vaporized.

The temperature for vaporization of the ethanol feedstock in the step A1 may be set in the range of −100 to 200° C., preferably 0 to 150° C., and even more preferably 25 to 100° C. When the temperature for vaporization of the ethanol feedstock is not lower than the lower limit of the above range, efficient vaporization is possible. When the temperature for vaporization of the ethanol feedstock is not higher than the upper limit of the above range, excessive heating is not necessary.

The step A may, as necessary, further include a step A2 of mixing at least one type of gas with the ethanol-containing gas obtained in the step A1 to adjust the concentration of ethanol in the ethanol-containing gas to fall within a range of 0.1 to 100% by volume.

The ethanol concentration of the ethanol-containing gas may be adjusted to fall within a range of 0.1 to 100% by volume, preferably 10 to 100% by volume, and more preferably 20 to 100% by volume. When the ethanol concentration of the ethanol-containing gas is not less than the lower limit of the above range, the yield of 1,3-butadiene improves.

As the gas (dilution gas) to be mixed with the ethanol-containing gas, a gas that does not adversely affect the conversion reaction from ethanol to 1,3-butadiene can be used, and examples thereof include noble gases such as nitrogen gas and argon gas. Of these, nitrogen gas and argon gas are preferable from the viewpoint of price and availability. With respect to the gas to be mixed with the ethanol-containing gas, a single type thereof may be used individually or two or more types thereof may be used in combination.

(Step B)

In the step B, the conversion reaction from ethanol to 1,3-butadiene may be a two-step reaction including the reactions represented by the following formulae (1) and (2).

$$CH_3CH_2OH \rightarrow CH_3CHO + H_2 \qquad (1)$$

$$CH_3CH_2OH + CH_3CHO \rightarrow CH_2=CH-CH=CH_2 + 2H_2O \qquad (2)$$

In the step B, it is preferable to use two or more parallel reactors for at least a part of the conversion reaction of converting ethanol in the ethanol-containing gas to 1,3-butadiene in the presence of a catalyst. When such two or more parallel reactors are used in the step B, the step D can be implemented, so that the yield of 1,3-butadiene improves.

Specifically, it is preferable to use such two or more parallel reactors in one or both of the first-stage conversion reaction and the second-stage conversion reaction.

In the step B, the two or more parallel reactors may be used for both the first-stage conversion reaction and the second-stage conversion reaction, or may be used for either one of the first-stage conversion reaction or the second-stage conversion reaction. Particularly, it is preferable to use the two or more parallel reactors for both the first-stage conversion reaction and the second-stage conversion reaction from the viewpoint of improving the yield of 1,3-butadiene.

The number of reactors installed in parallel in the step B can be appropriately set, and may be, for example, 2 to 5.

The step B for the two-step reaction may include, for example, the following steps B1 to B3.

Step B1: a step of supplying the ethanol-containing gas obtained in the step A to a first reactor and converting ethanol into acetaldehyde in the presence of a first catalyst under a pressure of 0 to 1.0 MPaG and at a temperature of 50 to 500° C.

Step B2: a step of supplying an intermediate gas containing ethanol and acetaldehyde obtained in the step B1 to a second reactor and converting the ethanol and the acetaldehyde into 1,3-butadiene in the presence of a second catalyst under a pressure of 0 to 1.0 MPaG and at a temperature of 50 to 500° C.

Step B3: a step of mixing one or both of a part of the ethanol-containing gas obtained in the step A1 and the acetaldehyde-containing gas obtained in the step C4 described below with the intermediate gas, thereby adjusting an ethanol/acetaldehyde molar ratio in the intermediate gas to 1 to 100.

The ethanol/acetaldehyde molar ratio in the intermediate gas is a ratio of the number of moles of ethanol to the number of moles of acetaldehyde in the intermediate gas.

As for the step B, it is preferable to use two or more parallel reactors in either one or both of the step B1 and the step B2, and it is more preferable to use two or more parallel first reactors in the step B1, while using two or more parallel second reactors in the step B2 as well.

In the step B1, a part of ethanol in the ethanol-containing gas supplied from the step A is converted to acetaldehyde in the presence of the first catalyst in the first reactor. As a consequence, an intermediate gas containing ethanol and acetaldehyde is generated.

The configuration of the first reactor is not particularly limited as long as the first reactor is capable of allowing the ethanol-containing gas to contact the first catalyst under a predetermined pressure and at a predetermined temperature. For example, the first reactor may have a configuration in which a first catalyst is filled in a reaction tube having a heat medium circulated in its side wall so as to form a reaction bed, and the supplied gas is allowed to contact the first catalyst of the reaction bed. The reaction bed is not particularly limited, and examples thereof include a fixed bed, a moving bed, and a fluidized bed.

The first catalyst is not particularly limited as long as it can promote the conversion reaction from ethanol to acetaldehyde, and examples thereof include a mixture of chromium oxide and copper oxide, zinc oxide, and a mixture of copper oxide and silicon oxide. Of these, a mixture of copper oxide and silicon oxide is preferable from the viewpoint of conversion rate to acetaldehyde. With respect to the first catalyst, a single type thereof may be used individually or two or more types thereof may be used in combination.

The pressure during the conversion reaction in the step B1 may be set in the range of 0 to 1.0 MPaG, preferably 0 to 0.5 MPaG, and more preferably 0 to 0.3 MPaG. When the pressure in the step B1 is not lower than the lower limit of the above range, the conversion rate to acetaldehyde improves. When the pressure in the step B1 is not higher than the upper limit of the above range, liquefaction during the reaction can be suppressed.

The temperature during the conversion reaction in the step B1 may be set in the range of 50 to 500° C., preferably 200 to 500° C., and even more preferably 250 to 350° C. When the temperature in the step B1 is not lower than the lower limit of the above range, the conversion rate to acetaldehyde improves. When the temperature in the step B1 is not higher than the upper limit of the above range, excessive energy consumption can be suppressed.

The conversion rate from ethanol to acetaldehyde in the step B1 is preferably 30 to 70%.

The conversion rate to aldehyde in the step B1 refers to a molar ratio (percentage) of the number of moles of ethanol consumed in the first reactor per unit time to the number of moles of ethanol in the ethanol-containing gas supplied to the first reactor per unit time. The number of moles of ethanol consumed in the first reactor per unit time is calculated by subtracting the number of moles of ethanol in the intermediate gas discharged from the first reactor per unit time from the number of moles of ethanol in the ethanol-containing gas supplied to the first reactor per unit time.

The selectivity for acetaldehyde in the conversion reaction in the step B1 is preferably 85% or more, and more preferably 90% or more. The selectivity for aldehyde in the step B1 refers to a molar ratio (percentage) of the number of moles of ethanol converted to acetaldehyde per unit time to the number of moles of ethanol consumed in the first reactor of the step B1 per unit time.

Examples of by-products that may be contained in the intermediate gas obtained in the step B1 include crotonaldehyde, butyraldehyde, ethyl acetate, acetic acid and the like.

In the step B2, ethanol and acetaldehyde in the intermediate gas supplied from the step B1 are converted to 1,3-butadiene in the presence of the second catalyst in the second reactor. As a consequence, a crude gas containing 1,3-butadiene is generated.

The configuration of the second reactor can be exemplified by those illustrated for the first reactor.

The second catalyst is not particularly limited as long as it can promote the conversion reaction of ethanol and acetaldehyde to 1,3-butadiene, and examples thereof include tantalum, zirconium, niobium, hafnium, magnesium, zinc, and silicon. Of these, hafnium is preferable from the viewpoint of the yield of 1,3-butadiene. With respect to the second catalyst, a single type thereof may be used individually or two or more types thereof may be used in combination.

The second catalyst may be used in the form of, for example, metals, oxides, or chlorides. Also, the second catalyst may be used in the form of, for example, a catalyst supported on a carrier, or a mixture of two or more kinds of catalysts.

The pressure during the conversion reaction in the step B2 may be set in the range of 0 to 1.0 MPaG, preferably 0 to 0.5 MPaG, and more preferably 0 to 0.3 MPaG. When the pressure in the step B2 is not lower than the lower limit of the above range, the yield of 1,3-butadiene improves. When the pressure in the step B2 is not higher than the upper limit of the above range, decrease in the 1,3-butadiene yield due to excessive reaction can be suppressed.

The temperature during the conversion reaction in the step B2 may be set in the range of 50 to 500° C., preferably 300 to 400° C., and even more preferably 320 to 370° C. When the temperature in the step B2 is not lower than the lower limit of the above range, the yield of 1,3-butadiene improves. When the temperature in the step B2 is not higher than the upper limit of the above range, decrease in the 1,3-butadiene yield due to excessive reaction can be suppressed.

The conversion rate of ethanol and acetaldehyde to 1,3-butadiene in the step B2 is preferably more than 30%, more preferably more than 40%, and even more preferably more than 50%.

The conversion rate to 1,3-butadiene in the step B2 refers to a molar ratio of the number of moles of ethanol and acetaldehyde consumed in the second reactor per unit time to the number of moles of ethanol and acetaldehyde in the intermediate gas supplied to the second reactor per unit time. The number of moles of ethanol and acetaldehyde consumed in the second reactor per unit time is calculated by subtracting the number of moles of ethanol and acetaldehyde in the crude product gas discharged from the second reactor per unit time from the number of moles of ethanol and acetaldehyde in the intermediate gas supplied to the second reactor per unit time.

The selectivity for 1,3-butadiene in the conversion reaction of the step B2 is preferably more than 60%, more preferably more than 70%, and even more preferably more than 80%. The selectivity for 1,3-butadiene in the step B2 refers to a molar ratio (percentage) of the number of moles of ethanol and acetaldehyde converted to 1,3-butadiene per unit time to the number of moles of ethanol and acetaldehyde consumed in the second reactor of the step B2 per unit time.

In the step B2, it is preferable that about 65 to 80% of acetaldehyde is converted to 1,3-butadiene.

Examples of by-products that may be contained in the crude gas obtained in the step B2 include ethylene, propylene, diethyl ether, ethyl acetate, butanol, hexanol, 1-butene, 2-butene, isobutylene, pentene, pentadiene, hexene, hexadiene and the like.

The step B3 is performed between the step B1 and the step B2. Hereinbelow, the ethanol/acetaldehyde molar ratio in the intermediate gas supplied to the second reactor is referred to as "molar ratio P".

The molar ratio P is adjusted in the step B3 to preferably 1 to 100, more preferably 1 to 50, even more preferably 1 to 20, and particularly preferably 1 to 10. When the molar ratio P is within the above range, the yield of 1,3-butadiene improves.

In the step B3, it is preferable that, based on the results of monitoring the molar ratio P with an analyzer, the amount of either one or both of a part of the ethanol-containing gas obtained in the step A1 and the acetaldehyde-containing gas to be mixed with the intermediate gas is adjusted. This enables the molar ratio P to be easily regulated to fall within the above range.

The analyzer can be exemplified by a process mass spectrometer.

In the step B3, as described above, a part of the ethanol-rich ethanol-containing gas, which is obtained in the step A1 included in the gas preparation step preceding the purification step and the conversion step, is directly mixed with the intermediate gas. This enables the molar ratio P to be adjusted to a relatively high value within the range mentioned above.

On the other hand, the ratio of ethanol tends to decrease after the step B1 in the conversion step. For example, when the acetaldehyde-containing gas obtained in the step C4 included in the purification step is to be reused and mixed with the intermediate gas, the ratio of ethanol decreases further, and it becomes difficult to control the ratio to a certain desired level. As a result, the molar ratio P significantly decreases, and the ratio is also liable to fluctuate, whereby it becomes difficult to control the molar ratio P to fall within the range described above, resulting in lower yield of 1,3-butadiene.

On the other hand, in the method of the present invention, the ethanol-containing gas supplied to the step B3 is increased by using the ethanol-rich ethanol-containing gas obtained in the step A1. As a consequence, it becomes easy to increase the ethanol ratio of the intermediate gas and control the above-mentioned molar ratio P to fall within the range described above while recovering and reusing the acetaldehyde-containing gas obtained in the step C4. Furthermore, it becomes possible to control the molar ratio P to a relatively high value within the above range. Therefore, the conversion efficiency is increased and the yield of 1,3-butadiene improves remarkably.

The step B preferably further includes the following step B4 for improving the yield of 1,3-butadiene.

Step B4: a step of separating hydrogen gas from the intermediate gas.

When the step B4 is performed, the step B4 may be performed before the step B3, or the step B4 may be performed after the step B3.

In the step B4, the method for separating hydrogen gas from the intermediate gas is not particularly limited, and can be exemplified by a method of separating the intermediate gas into a liquid containing ethanol and acetaldehyde and hydrogen gas by gas-liquid separation. In this instance, the liquid containing ethanol and acetaldehyde is heated, revaporized, and supplied to the second reactor as an intermediate gas.

The conditions for gas-liquid separation for separating hydrogen gas from the intermediate gas are preferably a pressure of 0 to 1.0 MPaG and a temperature of 0 to 100° C.

(Step C)

The step C includes at least one step selected from the group consisting of the following steps C1 to C4. Step C1: a step of converting butene (1-butene, 2-butene and isobutene) in the crude gas into 1,3-butadiene by dehydrogenation reaction.

Step C2: a step of separating hydrogen gas from the crude gas by gas-liquid separation to obtain a 1,3-butadiene-containing liquid.

Step C3: a step of distilling a liquefied product of the crude gas or the 1,3-butadiene-containing liquid to separate the liquefied product or the 1,3-butadiene-containing liquid into an ethylene-containing gas, a 1,3-butadiene-containing effluent, and an acetaldehyde-containing liquid.

Step C4: a step of distilling the acetaldehyde-containing liquid to separate the acetaldehyde-containing liquid into an acetaldehyde-containing gas and a residual liquid containing water.

In general, it is difficult to separate 1-butene, 2-butene, and isobutene from 1,3-butadiene by distillation or the like. In the step C1, the ratio of 1,3-butadiene can be increased by dehydrogenating 1-butene, 2-butene, and isobutene to convert them to 1,3-butadiene.

When both of the step C1 and the step C3 are performed in the step C, the step C1 may be performed before the step C3, or the step C1 may be performed after the step C3.

In the step C1, for example, the crude gas obtained in the step B or the 1,3-butadiene-containing effluent obtained in the step C3 is supplied to a fourth reactor, and 1-butene, 2-butene and isobutene are dehydrogenated and converted to 1,3-butadiene in the presence of a fourth catalyst under a pressure of −1.0 to 1.0 MPaG and at a temperature of 200 to 550° C.

The configuration of the fourth reactor in the step C1 can be exemplified by those illustrated for the first reactor.

The fourth catalyst may be any catalyst that promotes the dehydrogenation reaction of 1-butene, 2-butene, and isobutene, and examples thereof include molybdenum, tungsten, bismuth, tin, iron, and nickel. Among them, molybdenum is preferable as the fourth catalyst from the viewpoint of the yield of 1,3-butadiene. With respect to the fourth catalyst, a single type thereof may be used individually or two or more types thereof may be used in combination.

The pressure during the dehydrogenation reaction in the step C1 may be set in the range of −1.0 to 1.0 MPaG, preferably −0.5 to 0.5 MPaG, and more preferably −0.3 to 0.3 MPaG. When the pressure in the step C1 is not lower than the lower limit of the above range, the yield of 1,3-butadiene improves. When the pressure in the step C1 is not higher than the upper limit of the above range, the decrease in yield of 1,3-butadiene due to excessive reaction can be suppressed.

The temperature during the dehydrogenation reaction in the step C1 may be set in the range of 200 to 550° C., preferably 300 to 500° C., and more preferably 300 to 450° C. When the temperature in the step C1 is not lower than the lower limit of the above range, the yield of 1,3-butadiene improves. When the temperature in the step C1 is not higher than the upper limit of the above range, the decrease in the yield of 1,3-butadiene due to excessive reaction can be suppressed.

In the step C2, gas-liquid separation is performed on the crude gas obtained in the step B or the crude gas having gone through the step C1, to thereby separate hydrogen gas to obtain a 1,3-butadiene-containing liquid. When the ethanol-containing gas is diluted with a dilution gas such as nitrogen gas in the step A2, the dilution gas is separated together with the hydrogen gas in the step C2.

As for the conditions for gas-liquid separation of the crude gas, it is preferable that the pressure is 0 to 1.0 MPaG and the temperature is 0 to 100° C.

In the step C3, the liquefied crude gas obtained in the step B, the liquefied crude gas after the step C1, or the 1,3-butadiene-containing liquid after the step C2 is supplied to the distillation column for distillation. As a result, each of the above liquids is separated into an ethylene-containing gas, a 1,3-butadiene-containing effluent, and an acetaldehyde-containing liquid. More specifically, for example, using a dividing-wall distillation column, an ethylene-containing gas is withdrawn from the top of the column, an acetaldehyde-containing liquid is withdrawn from the bottom of the column, and a 1,3-butadiene-containing effluent is withdrawn from the middle section of the column. The step C3 may be performed using two distillation columns by a method in which the ethylene-containing gas is separated in the first distillation column, and the resulting is separated into the 1,3-butadiene-containing effluent and the acetaldehyde-containing liquid in the second distillation column.

The ethylene-containing gas includes propylene, methane, ethane and the like in addition to ethylene. When the liquefied crude gas obtained in the step B is distilled without performing the step C1, the dilution gas such as hydrogen gas and nitrogen gas is separated together with the ethylene-containing gas in the step C3.

The acetaldehyde-containing liquid contains ethanol, water and the like in addition to acetaldehyde.

When the step C3 is performed without performing the step C2, hydrogen gas is separated together with the ethylene-containing gas in the step C3. Further, when the ethanol-containing gas is diluted with a dilution gas such as nitrogen gas in the step A2, the dilution gas is separated together with the ethylene-containing gas in the step C3.

In the step C4, the acetaldehyde-containing liquid obtained in the step C3 is supplied to a distillation column and separated into an acetaldehyde-containing gas and a residual liquid containing water.

When the step C3 and the step C4 are performed in the step C, the step C3 and the step C4 need not be performed separately, and the step C3 and the step C4 may be performed simultaneously in one distillation column.

The amount of acetaldehyde in the acetaldehyde-containing gas obtained in the step C4 is preferably 10% by volume or more, more preferably 20% by volume or more, and even more preferably 40% by volume or more.

The purity of the purified 1,3-butadiene obtained in the step C is preferably 95.0% by mass or more, more preferably 99.0% by mass or more, and even more preferably 99.5% by mass or more.

(Step D)

When the conversion reaction is continued in the step B, carbon precipitation (caulking) occurs on the catalyst, and the catalytic activity decreases. On the other hand, in the step D, the catalyst in at least one of the two or more parallel reactors used in the step B is regenerated while continuing the step B. As a result, the catalyst can be regenerated without interrupting the production of 1,3-butadiene, and the yield of 1,3-butadiene improves.

The step D includes at least one step selected from the group consisting of the following steps D1 to D3. Step D1: a step of supplying an oxygen-containing gas having an oxygen concentration of 0.01 to 100% by volume to at least one of the two or more parallel reactors, and discharging a carbon dioxide-containing gas from the reactor, to thereby regenerate the catalyst, while continuing the step B.

Step D2: a step of taking out the catalyst from at least one of the two or more parallel reactors, and refilling the reactor with a catalyst regenerated by contacting it with an oxygen-containing gas outside the reactor, to thereby regenerate the catalyst, while continuing the step B.

Step D3: a step of replacing the catalyst in at least one of the two or more parallel reactors with an unused catalyst to regenerate the catalyst, while continuing the step B.

In the step D1 and the step D2, when the oxygen-containing gas is brought into contact with the catalyst, the carbon precipitated on the catalyst reacts with oxygen and is removed as carbon dioxide, so that the catalyst is regenerated. Even when sulfur components and nitrogen components adhere to the catalyst and the catalytic activity decreases, they react with oxygen and are removed as sulfur oxides and nitrogen oxides, so that the catalyst is regenerated.

In the steps D1 to D3, the conversion reaction in the presence of the catalyst is continued in the reactor(s) other than the reactor(s) being used for performing the catalyst regeneration treatment.

The oxygen concentration of the oxygen-containing gas is 0.01 to 100% by volume, preferably 1 to 100% by volume, more preferably 10 to 70% by volume, and even more preferably 20 to 50% by volume. When the oxygen concentration of the oxygen-containing gas is not less than the lower limit of the above range, the catalytic activity is easily restored and the yield of 1,3-butadiene improves. When the oxygen concentration of the oxygen-containing gas is not more than the upper limit of the above range, it is easy to prevent the oxygen concentration from becoming too high, and the likelihood of explosion is reduced.

Examples of the oxygen-containing gas include air, oxygen gas, and gas obtained by diluting oxygen gas with a dilution gas. Examples of the dilution gas include noble gases such as nitrogen gas and argon gas.

As the oxygen-containing gas, a gas obtained by diluting oxygen gas with a diluting gas is preferable in that the oxygen concentration can be adjusted to a desired value. From the viewpoint of availability, air is preferable as the oxygen-containing gas.

The catalyst regeneration treatment in the step D may be performed with respect to only one or both of the first catalyst in the step B1 and the second catalyst in the step B2.

When regenerating the first catalyst of the step B1, the step D includes at least one step selected from the group consisting of the following steps D11, D21 and D31.

Step D11: a step of supplying an oxygen-containing gas to at least one first reactor of the two or more parallel first reactors under a pressure of 0 to 1.0 MPaG and at a temperature of 0 to 500° C. and discharging a carbon dioxide-containing gas from the first reactor, to thereby regenerate the first catalyst, while continuing the step B.

Step D21: a step of taking out the first catalyst from at least one first reactor of the two or more parallel first reactors and refilling the first reactor with the first catalyst regenerated by contacting it with an oxygen-containing gas outside the first reactor, to thereby regenerate the first catalyst, while continuing the step B.

Step D31: a step of replacing the first catalyst in at least one first reactor of the two or more parallel first reactors with an unused first catalyst to regenerate the first catalyst, while continuing the step B.

In the step D11, the oxygen-containing gas is supplied to at least one first reactor of the two or more parallel first reactors. In the step D21, the first catalyst is taken out from at least one first reactor of the two or more parallel first reactors, and the first reactor is refilled with the first catalyst regenerated outside the first reactor. In the step D31, the first catalyst in at least one of the two or more parallel first reactors is replaced with an unused first catalyst. In either case, the ethanol-containing gas is continuously supplied to the remainder of the parallel first reactors.

In the first reactors used in the steps D11, D21 and D31, the first catalyst is regenerated and reactivated. The first catalyst of each first reactor can be regenerated without interrupting the continuous production of 1,3-butadiene by sequentially performing one or more catalyst regeneration treatments of the steps D11, D21 and D31 with respect to each of the two or more parallel first reactors. As a result, the decrease in the activity of the first catalyst in the step B1 can be suppressed, thereby improving the yield of 1,3-butadiene.

The specific mode for supplying the oxygen-containing gas to the first reactor in the step D11 can be exemplified by a mode in which the first reactor is separated from the production line and connected to a separately prepared regeneration treatment line to supply the oxygen-containing gas. Further, an oxygen-containing gas supply line and a carbon dioxide-containing gas discharge line may be added to the production line to supply the oxygen-containing gas to the first reactor on the production line.

The pressure during the catalyst regeneration treatment in the step D11 may be set in the range of 0 to 1.0 MPaG, preferably 0 to 0.5 MPaG, and more preferably 0 to 0.3 MPaG. When the pressure in the step D11 is not lower than the lower limit of the above range, the catalyst is sufficiently regenerated and the yield of 1,3-butadiene improves. When the pressure in the step D11 is not higher than the upper limit of the above range, it is easy to prevent the oxygen concentration from becoming too high, and the likelihood of explosion can be reduced.

The temperature during the catalyst regeneration treatment in the step D11 may be set in the range of 0 to 500° C., preferably 100 to 450° C., and more preferably 250 to 400° C. When the temperature in the step D11 is not lower than the lower limit of the above range, the catalyst is sufficiently regenerated and the yield of 1,3-butadiene improves. When the temperature in the step D11 is not higher than the upper limit of the above range, excessive energy consumption can be suppressed.

The preferred pressure and temperature conditions during the catalyst regeneration treatment in the step D21 are the same as those for the catalyst regeneration treatment in the step D11.

In the step D11, it is preferable to regulate the amount of oxygen in the first reactor based on the results of monitoring the oxygen concentration in the first reactor with an analyzer. This makes it possible to improve the yield of 1,3-butadiene while reducing the likelihood of explosion.

The method for controlling the amount of oxygen in the first reactor, when a less amount of oxygen is intended, can be exemplified by a method in which the oxygen concentration of the oxygen-containing gas is lowered, a method in which the supply amount of the oxygen-containing gas is reduced, and a method in which the amount of gas discharged from the first reactor is increased.

As the catalytic activity of the first catalyst decreases, the conversion rate of ethanol to acetaldehyde decreases, so that the molar ratio P in the intermediate gas supplied to the second reactor increases. Therefore, by monitoring the molar ratio P, decrease in the catalytic activity of the first catalyst can be detected. In the step D, it is preferable to carry out one or more of the steps D11, D21 and D31 depending on the results of monitoring the molar ratio P in the intermediate gas supplied to the second reactor with an analyzer. Consequently, the catalytic activity of the first catalyst can be efficiently restored without the molar ratio P in the intermediate gas supplied to the second reactor becoming too high, so that the yield of 1,3-butadiene improves.

In the step D of regenerating the first catalyst, it is preferable to discharge the intermediate gas from the first reactor, depending on the results of monitoring the hydrogen concentration in the first reactor with an analyzer. As a consequence, it is easy to prevent the hydrogen concentration from becoming too high, and the likelihood of explosion can be reduced. In addition, the first catalyst can be regenerated at an appropriate timing, and the yield of 1,3-butadiene improves.

The analyzer that monitors the hydrogen concentration in the first reactor can be exemplified by a process mass spectrometer.

When the second catalyst is to be regenerated in the step B2, the step D includes at least one step selected from the group consisting of the following steps D12, D22 and D32.

Step D12: a step of supplying an oxygen-containing gas to at least one second reactor of the two or more parallel second reactors under a pressure of 0 to 1.0 MPaG and at a temperature of 0 to 500° C. and discharging a carbon dioxide-containing gas from the second reactor, to thereby regenerate the second catalyst, while continuing the step B.

Step D22: a step of taking out the second catalyst from at least one second reactor of the two or more parallel second reactors and refilling the second reactor with the second catalyst regenerated by contacting it with an oxygen-containing gas outside the second reactor, to thereby regenerate the second catalyst, while continuing the step B.

Step D32: a step of replacing the second catalyst in at least one second reactor of the two or more parallel second reactors with an unused second catalyst to regenerate the second catalyst, while continuing the step B.

In the step D12, as in the step D11, the oxygen-containing gas is supplied to at least one second reactor of the two or more parallel second reactors. In the step D22, as in the step D21, the second catalyst is taken out from at least one second reactor of the two or more parallel second reactors, and the second reactor is refilled with the second catalyst regenerated outside the second reactor. In the step D32, as in the step 31, the second catalyst in at least one of the two or more parallel second reactors is replaced with an unused second catalyst. In either case, the intermediate gas is continuously supplied to the remainder of the parallel second reactors.

In the second reactors used in the steps D12, D22 and D32, the second catalyst is regenerated and reactivated. The second catalyst of each second reactor can be regenerated without interrupting the continuous production of 1,3-butadiene by sequentially performing one or more catalyst regeneration treatments of the steps D12, D22 and D32 with respect to each of the two or more parallel second reactors. As a result, decrease in the activity of the second catalyst in the step B2 can be suppressed, thereby improving the yield of 1,3-butadiene.

The specific mode for supplying the oxygen-containing gas to the second reactor in the step D12 can be exemplified by same mode as in the case of supplying the oxygen-containing gas to the first reactor illustrated for the step D11.

The pressure during the catalyst regeneration treatment in the step D12 may be set in the range of 0 to 1.0 MPaG, preferably 0 to 0.5 MPaG, and more preferably 0 to 0.3 MPaG. When the pressure in the step D12 is not lower than the lower limit of the above range, the catalyst is sufficiently regenerated and the yield of 1,3-butadiene improves. When the pressure in the step D12 is not higher than the upper limit of the above range, it is easy to prevent the oxygen concentration from becoming too high, and the likelihood of explosion can be reduced.

The temperature during the catalyst regeneration treatment in the step D12 may be set in the range of 0 to 500° C., preferably 200 to 500° C., and more preferably 300 to 450° C. When the temperature in the step D12 is not less than the lower limit of the above range, the catalyst is sufficiently regenerated and the yield of 1,3-butadiene improves. When the temperature in the step D12 is not higher than the upper limit of the above range, excessive energy consumption can be suppressed.

The preferred pressure and temperature conditions during the catalyst regeneration treatment in the step D22 are the same as those for the catalyst regeneration treatment in the step D12.

In the step D12, it is preferable to regulate the amount of oxygen in the second reactor based on the results of monitoring the oxygen concentration in the second reactor with an analyzer. This makes it possible to improve the yield of 1,3-butadiene while reducing the likelihood of explosion.

The method for regulating the amount of oxygen in the second reactor can be exemplified by those illustrated for regulating the amount of oxygen in the first reactor.

In the step D of regenerating the second catalyst, it is preferable to discharge the crude gas from the second reactor, depending on the results of monitoring the 1,3-butadiene concentration and the hydrogen concentration in the second reactor with an analyzer. It is also preferable to discharge the crude gas from the second reactor, depending on the results of monitoring the hydrogen concentration in the second reactor with an analyzer. As a consequence, the second catalyst can be regenerated at an appropriate timing, and the yield of 1,3-butadiene improves. Examples of the analyzer that monitors the 1,3-butadiene concentration and the hydrogen concentration in the second reactor include a process mass spectrometer and a gas chromatography analyzer.

The method of the present invention for producing 1,3-butadiene includes the above-mentioned steps A to C, and further includes the step D if necessary. The present invention can be practiced by appropriately selecting and combining the configurations described above for the steps A to D. Hereinbelow, specific explanations are made with respect to examples of embodiments of the method for producing 1,3-butadiene according to the present invention.

First Embodiment

FIG. 1 is a schematic view showing a production apparatus 100 used in the method for producing 1,3-butadiene according to the first embodiment.

In this context, the dimension and the like of the figures illustrated in the following explanations are mere examples, and the present invention is not necessarily limited thereto and can be practiced with appropriate modifications which do not affect the gist of the present invention.

The production apparatus 100 includes a feedstock container 102, a vaporizer 104, a dilution gas container 106, two or more parallel first reactors 108, two or more parallel second reactors 110, a gas-liquid separator 112, a first distillation column 114, a fourth reactor 116, a second distillation column 118, and a recovery unit 120.

The feedstock container 102 and the vaporizer 104 are connected by a pipe 10. A flow rate indicating controller 11 is provided on the pipe 10.

The vaporizer 104 and two or more parallel first reactors 108 are connected by a pipe 12 branched into two or more on its first reactor 108 side. The pipe 12 is provided, on its vaporizer 104 side as viewed from the junction of the branches, with a pressure indicating controller 14 that adjust the flow rate based on the pressure in the vaporizer 104, a mixer 16, and a heat exchanger 18, and a temperature indicating controller 20 in this order as viewed from the vaporizer 104 side. A valve 22 is provided at each branch of the pipe 12.

The dilution gas container 106 is connected by a pipe 24 between the pressure indicating controller 14 provided on the pipe 12 and the mixer 16. The pipe 24 is provided with a flow rate indicating controller 26.

The two or more parallel first reactors 108 and the two or more parallel second reactors 110 are connected by a pipe 28 having branches on both ends. A valve 30 is provided at each branch of the pipe 28 on its first reactor 108 side, a valve 32 is provided at each branch of the pipe 28 on its second reactor 110 side, and an analyzer 34 is provided between the branches. Further, a pipe 36 is provided which branches off from between the vaporizer 104 on the pipe 12 and the pressure indicating controller 14 and is connected to the pipe 28 between its branch on the second reactor 110 side and the analyzer 34. The pipe 36 is provided with a flow rate indicating controller 38, and the flow rate in the pipe 36 can be adjusted based on the analysis results obtained by the analyzer 34.

The two or more parallel second reactors 110 and a gas-liquid separator 112 are connected by a pipe 40. A valve 42 is provided at each branch of the pipe 40 on the second reactor 110 side, and a heat exchanger 44 is provided at a position closer to the gas-liquid separator 112.

The gas-liquid separator 112 and the first distillation column 114 are connected by a pipe 46. The pipe 46 is provided with a pump 48 and a level indicating controller 50 for regulating the flow rate depending on the liquid level in the gas-liquid separator 112 in this order as viewed from the gas-liquid separator 112 side.

A pipe 52 is connected to the top of the first distillation column 114. Further, a pipe 54 that is connected to the gas phase portion of the gas-liquid separator 112 and joins the pipe 52 is provided.

The intermediate section of the first distillation column 114 and the fourth reactor 116 are connected by a pipe 56. The fourth reactor 116 and the recovery unit 120 are connected by a pipe 58.

The bottom of the first distillation column 114 and the second distillation column 118 are connected by a pipe 60. The top of the second distillation column 118 is connected by a pipe 62 with the connecting portion between the analyzer 34 and a joint where the pipe 28 and the pipe 36 meet. A pipe 64 is connected to the bottom of the second distillation column 118.

Hereinbelow, a method for producing 1,3-butadiene according to the first embodiment using the production apparatus 100 is described.

The ethanol feedstock as a liquid is transferred from the feedstock container 102 to the vaporizer 104 through the pipe 10, and the ethanol feedstock is vaporized under a pressure of −1.0 to 1.0 MPaG and at a temperature of −100 to 200° C. to obtain an ethanol-containing gas (step A1). The ethanol-containing gas is transferred from the vaporizer 104 to the pipe 12, into which nitrogen gas (dilution gas) is mixed from the dilution gas-container 106 through the pipe 24, and the resulting is mixed by the mixer 16. Then, the ethanol concentration of the ethanol-containing gas is adjusted to fall within a range of 0.1 to 100% by volume (step A2).

The ethanol-containing gas having its ethanol concentration adjusted is heated by the heat exchanger 18 and supplied to the two or more parallel first reactors 108. In each of the first reactors 108, ethanol is converted to acetaldehyde in the presence of the first catalyst under a pressure of 0 to 1.0 MPaG and at a temperature of 50 to 500° C. (step B1). An intermediate gas containing ethanol and acetaldehyde generated in each first reactor 108 is transferred to the pipe 28.

A part of the ethanol-containing gas obtained in the vaporizer 104 (step A1) is mixed with the intermediate gas through the pipe 36. Further, the acetaldehyde-containing gas withdrawn from the top of the second distillation column 118 (step C4) described below to the pipe 62 is also mixed with the intermediate gas. The molar ratio P in the intermediate gas supplied to the second reactor 110 is analyzed by the analyzer 34. Based on the results, the flow rate of the ethanol-containing gas in the pipe 36 is adjusted by the flow rate indicating controller 38, and the molar ratio P of the intermediate gas supplied to the second reactor 110 is adjusted to fall within a range of 1 to 100 (step B3).

The intermediate gas with its molar ratio P adjusted is supplied to the two or more parallel second reactors 110. In each of the second reactors 110, ethanol and acetaldehyde are converted to 1,3-butadiene in the presence of the second catalyst under a pressure of 0 to 1.0 MPaG and at a temperature of 50 to 500° C. (step B2).

The crude gas containing 1,3-butadiene is transferred from each second reactor 110 to the pipe 40, cooled by the heat exchanger 44, and supplied to the gas-liquid separator 112. In the gas-liquid separator 112, the crude gas is gas-liquid separated into hydrogen gas, nitrogen gas (dilution gas) and 1,3-butadiene-containing liquid (step C2). The pump 48 is driven to supply the 1,3-butadiene-containing liquid from the gas-liquid separator 112 to the first distillation column 114 through the pipe 46 for distillation. An ethylene-containing gas is withdrawn from the top of the first distillation column 114 into the pipe 52, an acetaldehyde-containing liquid is withdrawn from the bottom of the column into the pipe 60, and a 1,3-butadiene-containing effluent is withdrawn from the middle section of the column into the pipe 56 (step C3). The ethylene-containing gas withdrawn into the pipe 52 is combined with the hydrogen gas and the nitrogen gas (dilution gas) withdrawn from the gas phase portion of the gas-liquid separator 112 into the pipe 54 and disposed as waste gas.

The 1,3-butadiene-containing effluent withdrawn into the pipe 56 is supplied to the fourth reactor 116, and 1-butene, 2-butene and isobutene in the 1,3-butadiene-containing effluent are dehydrogenated in the presence of a fourth catalyst to be converted to 1,3-butadiene (step C1). Purified 1,3-butadiene is transferred from the fourth reactor 116 to the recovery unit 120 by the pipe 58 for recovery.

The acetaldehyde-containing liquid withdrawn from the bottom of the first distillation column 114 into the pipe 60 is supplied to the second distillation column 118 for distillation. The residual liquid containing water is withdrawn from the bottom of the second distillation column 118 into the pipe 64, and the acetaldehyde-containing gas is withdrawn from the column top into the pipe 62 (step C4). The acetaldehyde-containing gas withdrawn into the pipe 62 is mixed with the intermediate gas as described above (step B3). The residual liquid containing water withdrawn into the pipe 64 is treated as waste liquid.

For example, the valves 22 and 30 on both sides of at least one of the two or more parallel first reactors 108 are closed, and the reactor is disconnected from the production line. An oxygen-containing gas is supplied to the disconnected first reactor 108 under a pressure of 0 to 1.0 MPaG and at a temperature of 0 to 500° C. while discharging a carbon dioxide-containing gas from the first reactor 108, thereby regenerating the first catalyst. Alternatively, the first catalyst is taken out from the first reactor 108, which is then refilled with the first catalyst regenerated outside the first reactor 108 or an unused first catalyst, to thereby regenerate the first catalyst. In this process, in the remainder of the first reactors 108, the conversion reaction from ethanol to acetaldehyde is continued, and 1,3-butadiene is continuously produced (steps D11, D21, and D31). The first reactor 108 after the catalyst regeneration treatment is reconnected to the production line, and the valves 22 and 30 on both sides thereof are opened to restart the conversion reaction (step B1).

For example, the valves 32 and 42 on both sides of at least one of the two or more parallel second reactors 110 are closed, and the reactor is disconnected from the production line. An oxygen-containing gas is supplied to the disconnected second reactor 110 under a pressure of 0 to 1.0 MPaG and at a temperature of 0 to 500° C. while discharging a carbon dioxide-containing gas from the second reactor 110, thereby regenerating the second catalyst. Alternatively, the second catalyst is taken out from the second reactor 110, which is then refilled with the second catalyst regenerated outside the second reactor 110 or an unused second catalyst, to thereby regenerate second first catalyst. In this process, in the remainder of the second reactors 110, the conversion reaction from ethanol and acetaldehyde to 1,3-butadiene is continued, and 1,3-butadiene is continuously produced (steps D12, D22, and D32). The second reactor 110 after the catalyst regeneration treatment is reconnected to the production line, and the valves 32 and 42 on both sides thereof are opened to restart the conversion reaction (step B2).

In the first embodiment, any one of steps D11, D21, D31, D12, D22 and D32 may be performed, or two or more thereof may be appropriately combined.

In the production apparatus 100 having the above configuration, it is preferable to install a dust collector (not shown) to prevent the first catalyst from intruding into the second reactor 110 somewhere in the path of the pipe 28 connecting the first reactor 108 and the second reactor 110. Further, it is more preferable to install such a dust collector between the first reactor 108 and the junction with the pipe 62 in the path of the pipe 28.

By installing such a dust collector, it is possible to suppress the conversion reaction from ethanol to acetaldehyde in the second reactor 110, and stably maintain the conversion to 1,3-butadiene by the second catalyst that requires ethanol.

The dust collector as described above is not particularly limited, and examples thereof include a cyclone, a bag filter, and a packed bed filter.

Further, in the production apparatus 100, in order to prevent the first catalyst or the second catalyst from flowing out to the downstream side of the first reactor 108 or the second reactor 110, it is preferable to install a catalyst holding unit (not shown) on the downstream side of these reactors, specifically, on the pipe 28 and the pipe 40.

By installing such a catalyst holding unit, the first catalyst and the second catalyst flowing out from the first reactor 108 or the second reactor 110 can be prevented from being accumulated at a location other than inside of these reactors, e.g., in the pipes. This enables the suppression of generation of carbon-containing materials or the suppression of decrease in the yield of 1,3-butadiene, which is caused by the conversion reaction of ethanol or ethanol and acetaldehyde to 1,3-butadiene occurring at a location other than the reactors.

The catalyst holding unit as described above is not particularly limited, and examples thereof include a support grid, a perforated plate, and alumina balls.

Second Embodiment

Figure 2:
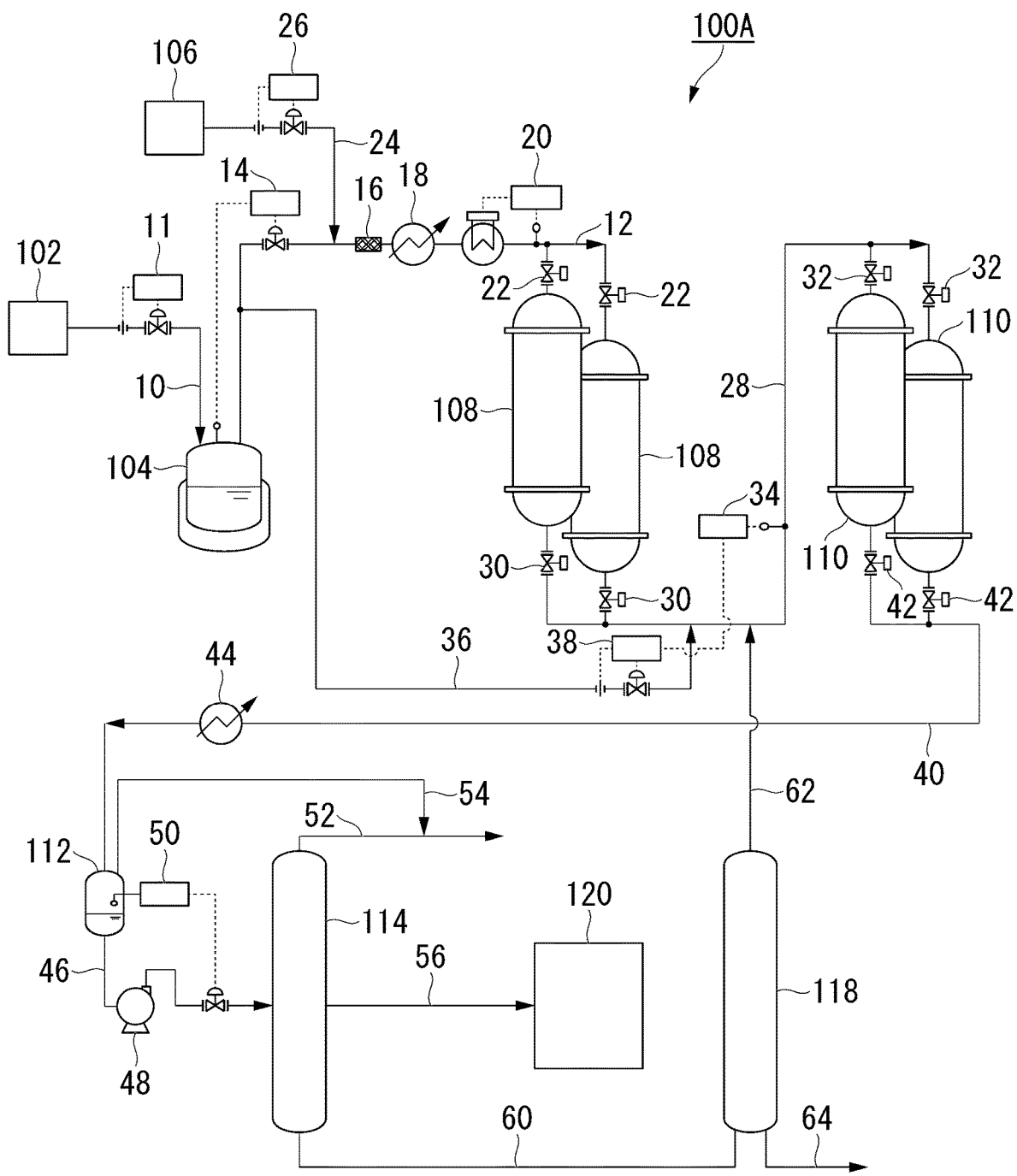
FIG. 2 is a schematic view showing a production apparatus used in the method for producing 1,3-butadiene according to the second embodiment.

FIG. 2 is a schematic view showing a production apparatus 100A used in the method for producing 1,3-butadiene according to the second embodiment.

The production apparatus 100A has the same configuration as the production apparatus 100 except that the fourth reactor 116 is not provided and the middle section of the first distillation column 114 and the recovery portion 120 are connected by a pipe 56.

The method for producing 1,3-butadiene in the second embodiment using the production apparatus 100A can be performed in the same manner as in the first embodiment using the production apparatus 100, except that the step C1 is omitted.

Third Embodiment

Figure 3:
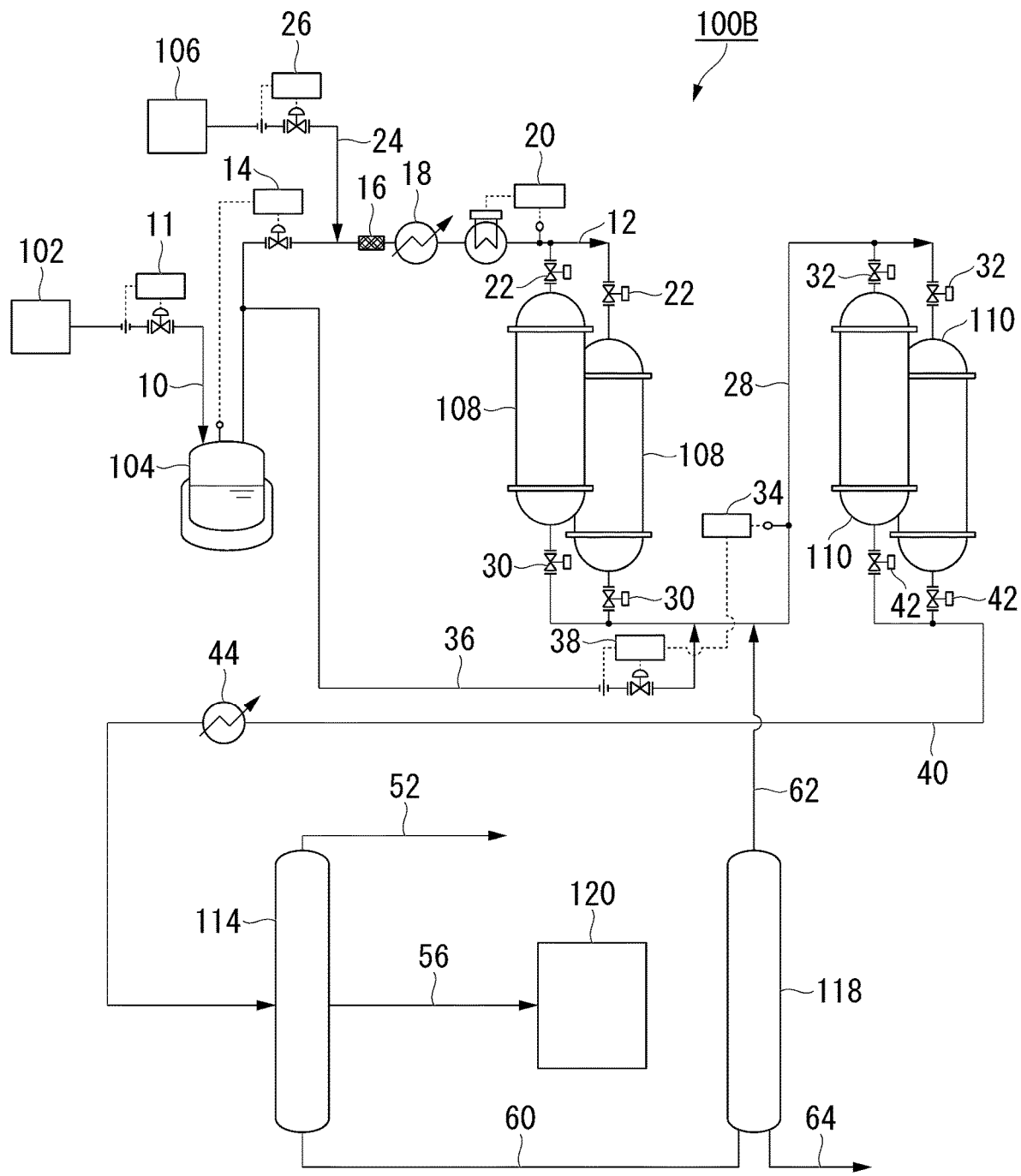
FIG. 3 is a schematic view showing a production apparatus used in the method for producing 1,3-butadiene according to the third embodiment.

FIG. 3 is a schematic view showing a production apparatus 100B used in the method for producing 1,3-butadiene according to the third embodiment.

The production apparatus 100B has the same configuration as the production apparatus 100 except for the following aspects. The production apparatus 100B does not include the gas-liquid separator 112, and two or more parallel second reactors 110 and the first distillation column 114 are connected by a pipe 40. The production apparatus 100B does not include the fourth reactor 116, and the middle section of the first distillation column 114 and the recovery unit 120 are connected by a pipe 56.

The method for producing 1,3-butadiene according to the third embodiment using the production apparatus 100B can be performed in the same manner as in the first embodiment using the production apparatus 100, except that the steps C1 and C2 are omitted. Hydrogen gas and nitrogen gas (dilution gas) are withdrawn from the top of the first distillation column 114 together with the ethylene-containing gas.

As described above, since the method of the present invention for producing 1,3-butadiene implement the steps A to C, 1,3-butadiene can be continuously produced in high yield.

The method for producing 1,3-butadiene according to the present invention is not limited to the above-described embodiments, and the configurations described for the respective steps can be appropriately combined. Further, the features of the embodiments described above can be appropriately replaced by known equivalents as long as such replacement does not deviate from the essence of the present invention. Furthermore, for example, it is possible to increase the yield of 1,3-butadiene by appropriately combining the configurations of the other steps without selecting the step B3.

EXAMPLES

Hereinbelow, the present invention will be described in detail with reference to Examples which, however, should not be construed as limiting the present invention.

In the Examples, process simulations were performed using a software of Aspen Technology, Inc., with respect to the configuration of the production apparatus and process flow shown in FIG. 1.

Comparative Example 1

In Comparative Example 1, a simulation of the continuous production of 1,3-butadiene was performed following the procedure and conditions as specified in claim 1 of the present application, except that the conversion step follows a process flow lacking the step B3 as specified in claim 1 of the application, i.e., process flow lacking the step of mixing one or both of a part of the ethanol-containing gas obtained in the step A1 and the acetaldehyde-containing gas obtained in the step C4 with the intermediate gas, thereby adjusting an ethanol/acetaldehyde molar ratio in the intermediate gas to 1 to 100.

In Comparative Example 1, the continuous feeding of ethanol-containing gas at 15 kL/h in the conversion step resulted in the ethanol/acetaldehyde molar ratio of 0.6 in the intermediate gas, thereby producing a 1,3-butadiene-containing effluent of 5.29 t/h after a predetermined period of time.

Example 1

In Example 1, a simulation of the continuous production of 1,3-butadiene was performed following the requirements of claim 1 of the present application, employing a process flow in which the conversion step further includes the step B3 described above.

In Example 1, the continuous feeding of ethanol-containing gas at 15 kL/h in the conversion step resulted in the ethanol/acetaldehyde molar ratio of 1 in the intermediate gas, thereby producing a 1,3-butadiene-containing effluent of 5.33 t/h after a predetermined period of time.

The results of the above Examples clarified that 1,3-butadiene can be continuously produced in high yield by adopting the process flow including the conversion step specified in the present invention.

INDUSTRIAL APPLICABILITY

The method of the present invention for producing 1,3-butadiene can continuously produce 1,3-butadiene in high yield and, hence, is particularly suitable for a process for producing a raw material of styrene-butadiene rubber (SBR) and the like.

DESCRIPTION OF THE REFERENCE SIGNS 100,100A,100B Production apparatus
102 Feedstock container
104 Vaporizer
106 Dilution gas container
108 First reactor
110 Second reactor
112 Gas-liquid separation unit
114 First distillation column
116 Fourth reactor
118 Second distillation column
120 Recovery unit

The invention claimed is:
1. A method for continuously producing 1,3-butadiene from an ethanol feedstock containing ethanol, comprising:

a gas preparation step of preparing an ethanol-containing gas from the ethanol feedstock; a conversion step of converting ethanol in the ethanol-containing gas to 1,3-butadiene in the presence of a catalyst; and a purification step of purifying a crude gas containing the 1,3-butadiene obtained in the conversion step to obtain a purified 1,3-butadiene, wherein the gas preparation step comprises a step A1 of vaporizing the ethanol feedstock to obtain the ethanol-containing gas under a pressure of −1.0 to 1.0 MPaG and at a temperature of −100 to 200° C., the purification step comprises a step C3 of distilling a liquefied product of the crude gas or the 1,3-butadiene-containing liquid to separate the liquefied product or the 1,3-butadiene-containing liquid into an ethylene-containing gas, a 1,3-butadiene-containing effluent, and an acetaldehyde-containing liquid; and a step C4 of distilling the acetaldehyde-containing liquid to separate the acetaldehyde-containing liquid into an acetaldehyde-containing gas and a residual liquid containing water, wherein the purification step optionally further comprises at least one step selected from the group consisting of a step C1 of converting butene in the crude gas into 1,3-butadiene by dehydrogenation reaction; and a step C2 of separating hydrogen gas from the crude gas by gas-liquid separation to obtain a 1,3-butadiene-containing liquid, and the conversion step comprises a step B1 of supplying the ethanol-containing gas obtained in the step A1 to a first reactor and converting ethanol into acetaldehyde in the presence of a first catalyst under a pressure of 0 to 1.0 MPaG and at a temperature of 50 to 500° C., a step B2 of supplying an intermediate gas containing ethanol and acetaldehyde obtained in the step B1 to a second reactor and converting the intermediate gas into 1,3-butadiene under a pressure of 0 to 1.0 MPaG and at a temperature of 50 to 500° C. in the presence of a second catalyst, and a step B3 of mixing both of a part of the ethanol-containing gas obtained in the step A1 and the acetaldehyde-containing gas obtained in the step C4 with the intermediate gas, thereby increasing an ethanol ratio in the intermediate gas so as to adjust an ethanol/acetaldehyde molar ratio in the intermediate gas to 1 to 100, wherein an amount of either one or both of the ethanol-containing gas and the acetaldehyde-containing gas which are mixed with the intermediate gas in the step B3 is adjusted, based on results of monitoring the ethanol/acetaldehyde molar ratio in the intermediate gas supplied to the second reactor by an analyzer connected between the second reactor and a position where the ethanol-containing gas and the acetaldehyde-containing gas are mixed with the intermediate gas.

2. The method according to claim 1, wherein the conversion step further comprises a step B4 of separating hydrogen gas from the intermediate gas.

3. The method according to claim 1, wherein the intermediate gas is discharged from the first reactor, based on results of monitoring a hydrogen concentration in the first reactor by an analyzer.

4. The method according to claim 1, wherein the crude gas is discharged from the second reactor, based on results of monitoring a 1,3-butadiene concentration and a hydrogen concentration in the second reactor with an analyzer.

5. The method according to claim 1, wherein the gas preparation step further comprises a step A2 of mixing at least one type of gas with the ethanol-containing gas to adjust the concentration of ethanol in the ethanol-containing gas to fall within a range of 0.1 to 100% by volume.

* * * * *